United States Patent
Horita et al.

(10) Patent No.: US 9,604,012 B2
(45) Date of Patent: Mar. 28, 2017

(54) BARREL WITH CAP, PRE-FILLED SYRINGE, AND CAP WITH CONNECTOR

(75) Inventors: Taiji Horita, Ibaraki (JP); Norihiko Asahi, Ibaraki (JP); Ippei Matsumoto, Ibaraki (JP); Kensuke Taniguchi, Ibaraki (JP); Takeshi Karasawa, Ibaraki (JP); Akemi Sasaki, Ibaraki (JP)

(73) Assignee: Taisei Kako Co., Ltd., Osaka (JP)

(*) Notice: Subject to any disclaimer, the term of this patent is extended or adjusted under 35 U.S.C. 154(b) by 729 days.

(21) Appl. No.: 14/009,582

(22) PCT Filed: Apr. 20, 2011

(86) PCT No.: PCT/JP2011/059701
§ 371 (c)(1),
(2), (4) Date: Oct. 3, 2013

(87) PCT Pub. No.: WO2012/144026
PCT Pub. Date: Oct. 26, 2012

(65) Prior Publication Data
US 2014/0025017 A1    Jan. 23, 2014

(51) Int. Cl.
*A61M 5/34* (2006.01)
*A61M 5/31* (2006.01)

(52) U.S. Cl.
CPC .......... *A61M 5/344* (2013.01); *A61M 5/347* (2013.01); *A61M 2005/3104* (2013.01)

(58) Field of Classification Search
CPC ...... A61M 5/344; A61M 5/345; A61M 5/347; A61M 5/348; A61M 2005/3104;
(Continued)

(56) References Cited

U.S. PATENT DOCUMENTS

| 6,520,935 B1 | 2/2003 | Jansen et al. |
| 2006/0106349 A1 | 5/2006 | Kito et al. |

(Continued)

FOREIGN PATENT DOCUMENTS

| JP | H8-215307 A | 8/1996 |
| JP | 2004-160206 | 6/2004 |

(Continued)

OTHER PUBLICATIONS

International Preliminary Report on Patentability issued Oct. 22, 2013 in connection with related PCT/ JP2011/059701 and translation of the same.

(Continued)

*Primary Examiner* — Kami A Bosworth
(74) *Attorney, Agent, or Firm* — Berliner & Associates

(57) ABSTRACT

A barrel with a cap, a pre-filled syringe, and a cap with a connector that accommodate connection-receiving bodies of the Luer lock type and of the slip-in type, are provided. Some versions include: a connector (3) detachably coupled to a cap (2) so as to be separated from the barrel (1) together with the cap (2) when the connector (3) is located at an initial position where the connector (3) is attached to a barrel (1) via the cap (2); and a connector-side engaging part (33) that engages a barrel-side engaging part (13) of the barrel (1) when the connector (3) is located at an attached position that is closer to a proximal end in an axial direction of the barrel (1) than the initial position, allowing the connector (3) to remain attached to the barrel (1) by being detached from the cap (2) separated from a nozzle (11).

7 Claims, 13 Drawing Sheets

(58) Field of Classification Search
CPC .. A61M 2005/3106; A61M 2005/3118; A61M 2005/312
See application file for complete search history.

(56) References Cited

U.S. PATENT DOCUMENTS

2011/0015578 A1   1/2011   Lowke
2012/0018318 A1   1/2012   Otsuka et al.

FOREIGN PATENT DOCUMENTS

| JP | 2006-160206 | 6/2004 |
|----|-------------|--------|
| JP | 2005-110873 A | 4/2005 |
| JP | 2005-296140 | 10/2005 |
| JP | 2006-166961 | 6/2006 |
| JP | 2008-246070 A | 10/2008 |
| WO | WO2010/114100 A1 | 10/2010 |

OTHER PUBLICATIONS

European Search Report issued Nov. 14, 2014 in connection with related European Patent Appl. No. 11863841.0.

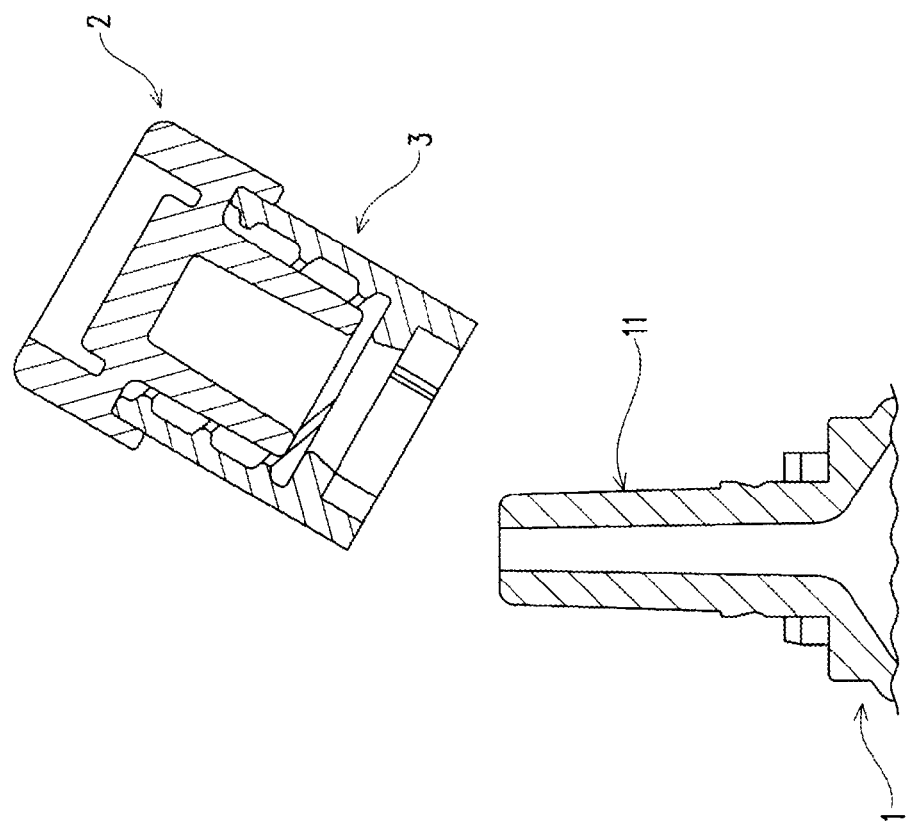
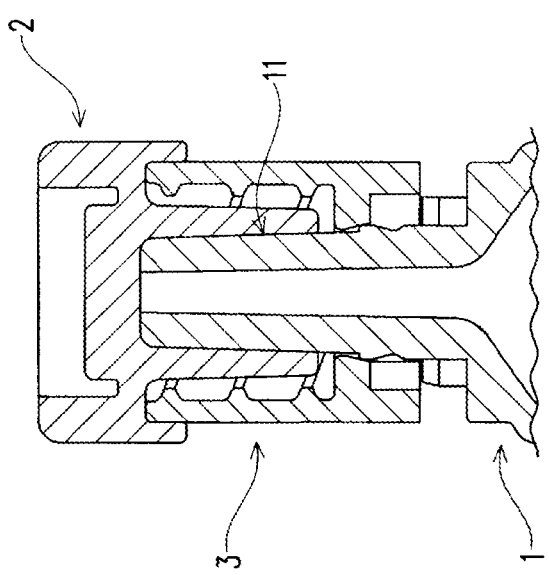

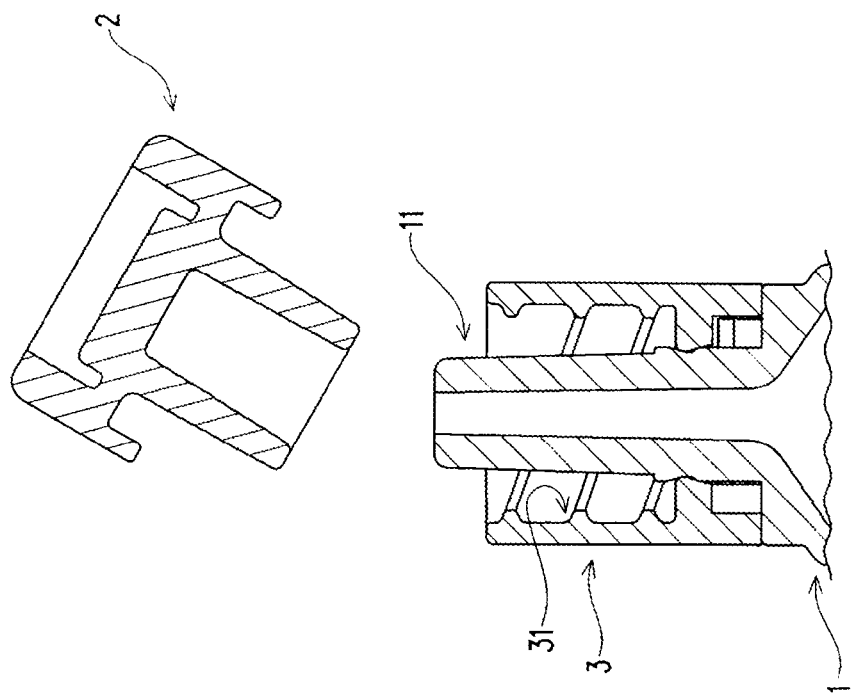
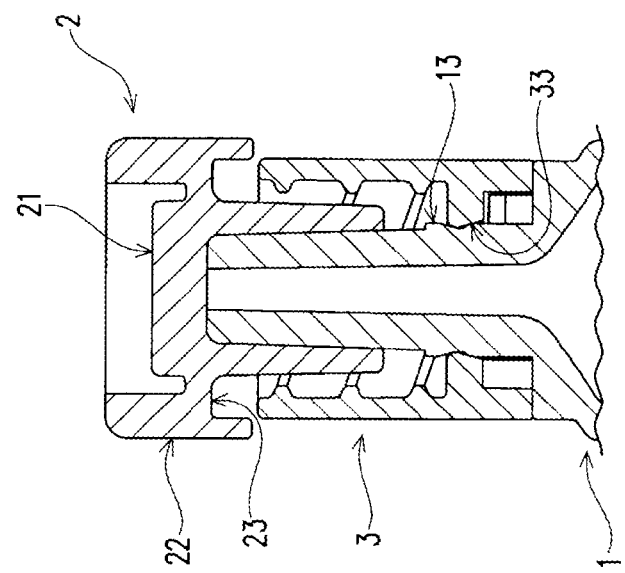
FIG. 7(a)
FIG. 7(b)

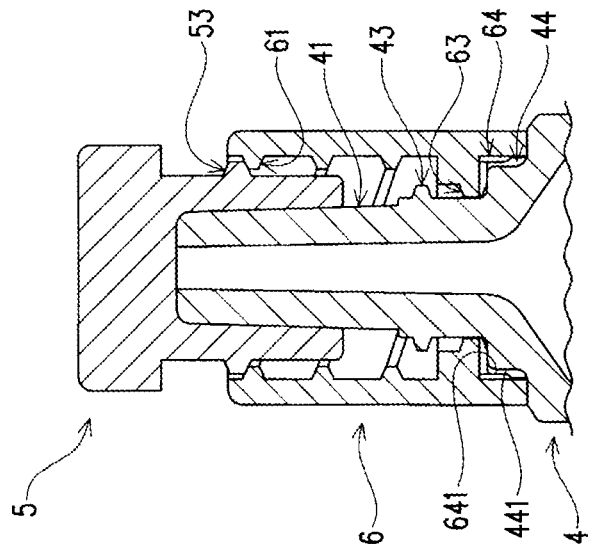
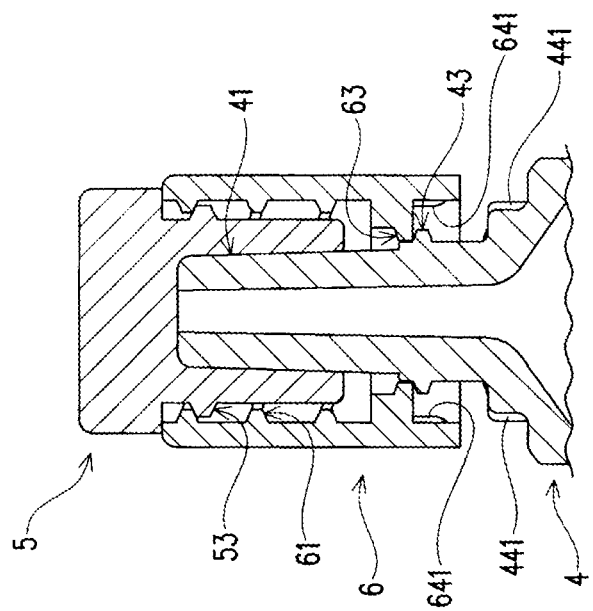

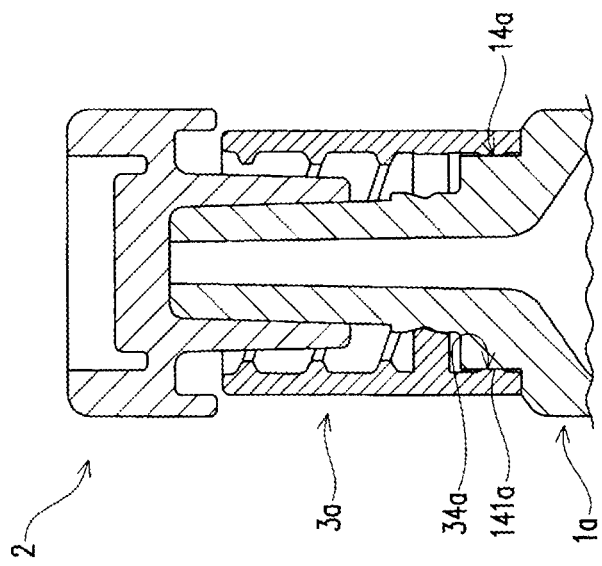
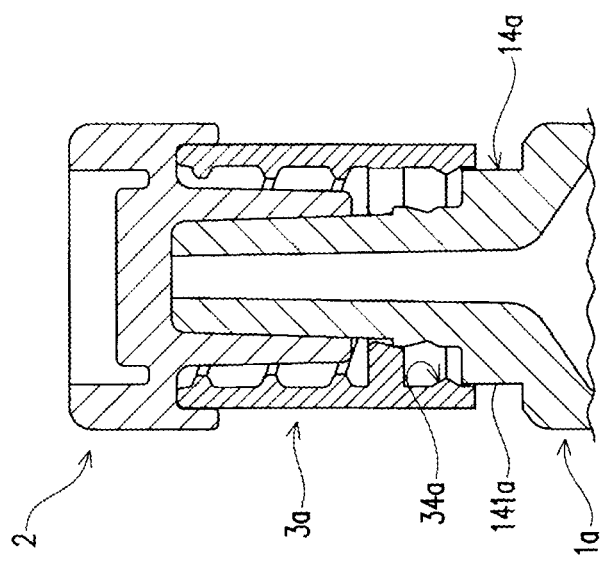

BARREL WITH CAP, PRE-FILLED SYRINGE, AND CAP WITH CONNECTOR

FIELD

The present invention relates to a barrel with a cap which includes: a cap that sealingly closes a nozzle provided at the distal end of the barrel; and a connector having a threaded portion that threadedly engages a connection-receiving body to be connected to the nozzle, and further relates to a pre-filled syringe including the barrel with a cap. Furthermore, the present invention relates to a cap with a connector, attached to the barrel, including the aforementioned cap and the aforementioned connector.

BACKGROUND

As a syringe provided with a barrel and a plunger, a syringe including a cap that sealingly closes a nozzle provided at the distal end of the barrel and a connector having a threaded portion that threadedly engages a connection-receiving body to be connected to the nozzle is conventionally known (e.g., Patent Literature 1). According to such a syringe, the cap is separated from the nozzle, and the threaded portion of the connector threadedly engages the threaded portion of the connection-receiving body. Thus, the connection-receiving body is securely connected to the nozzle via the connector.

CITATION LIST

Patent Literature

Patent Literature 1: JP 2006-166961 A

SUMMARY

Technical Problem

As such a connection-receiving body to be connected to the nozzle, there are injection needles, access ports (means for co-injection into an infusion line), or the like, of so-called Luer lock (screw-in) type, which have a threaded portion that threadedly engages the threaded portion of the connector, as mentioned above, while there are injection needles, access ports, or the like, of so-called slip-in (insertion) type, which have no threaded portion and are connected to the nozzle only by insertion of the nozzle thereinto. The syringe according to Patent Literature 1 is available for connection-receiving bodies of the Luer lock type, but not available for connection-receiving bodies of the slip-in type, which is a problem.

In view of such a circumstance, it is therefore an object of the present invention to provide a barrel with a cap, a pre-filled syringe, and a cap with a connector that are available for both connection-receiving bodies of the Luer lock type and connection-receiving bodies of the slip-in type.

Solution to Problem

According to the present invention, there is provided a barrel with a cap including: a tubular barrel having a nozzle at its distal end; a cap to be attached to the nozzle so as to sealingly close the nozzle; a tubular connector into which the nozzle is inserted, the connector having a threaded portion for threadedly engaging a connection-receiving body to be connected to the nozzle, wherein the connector is detachably coupled to the cap and is separated from the barrel together with the cap when the connector is located at an initial position in which the connector is attached to the barrel via the cap, and the connector includes a connector-side engaging part that engages the barrel when the connector is located at an attached position that is located closer to a proximal end in an axial direction of the barrel than the initial position is, thereby allowing the connector to remain attached to the barrel by being detached from the cap separated from the nozzle.

According to the barrel with a cap of the present invention, when the connector that is detachably coupled to the cap is located at the initial position, the connector is attached to barrel via the cap. Thereby, when the cap is separated from the nozzle, the connector is separated from the barrel integrally with the cap.

Meanwhile, when the connector is located at the attached position that is closer to the proximal end in the axial direction of the barrel than the initial position is, the connector-side engaging part of the connector engages the barrel. Thus, the cap is directly attached onto the barrel, and therefore when the cap is separated from the nozzle, only the connector detached from the cap remains attached to the barrel.

Accordingly, in the case of connection-receiving bodies of the slip-in type, the connector can be separated from the nozzle integrally with the cap by separating the cap from the nozzle when the connector is located at the initial position. Meanwhile, in the case of connection-receiving bodies of the Luer lock type, the connector is located at the attached position so that the connector is directly attached onto the barrel, and thereafter the cap is separated from the nozzle, thereby allowing only the connector to remain attached to the barrel.

Moreover, in the case of connecting a connection-receiving body of the Luer lock type to the nozzle, it is possible to prevent the connection receiving body from being connected to the nozzle, with the connector having a clearance for movement or being loosened with respect to the barrel, by attaching the connector to the barrel immediately before the connection receiving body is connected to the nozzle. Accordingly, the connection-receiving body can be securely connected to the nozzle.

In the barrel with a cap according to the present invention, the barrel may include a barrel-side engaging part that engages the connector-side engaging part when the connector is pressed down from the initial position to the attached position, so that the connector is fixed at the attached position.

According to the barrel with a cap having such a configuration, the connector is pressed down from the initial position to the attached position, whereby the barrel-side engaging part engages the connector-side engaging part. Thus, the connector is fixed at the attached position. Thus, the connector is directly attached onto the barrel, and therefore when the cap is separated from the nozzle, only the connector detached from the cap remains attached to the barrel.

In the barrel with a cap according to the present invention, the cap may include: a sealing part that sealingly closes the nozzle; a coupling part that is coupled to the connector; and a connecting part that connects the sealing part and the coupling part to each other in relatively displaceable manner in the axial direction of the barrel.

According to the barrel with a cap having such a configuration, the sealing part that sealingly closes the nozzle and the coupling part that is coupled to the connector are connected to each other via the connecting part in relatively displaceable manner in the axial direction of the barrel. Accordingly, when the connector is pressed down from the initial position to the attached position, the coupling part is relatively displaced in the axial direction of the barrel with respect to the sealing part, which enables the sealing part to keep sealingly closing the nozzle.

The barrel with a cap according to the present invention may be configured so that: the connector-side engaging part is threaded: and the barrel includes a barrel-side engaging part that is threaded to cause the connector to be displaced from the initial position to the attached position, as the threaded engagement with the connector-side engaging part proceeds, so that the connector is fixed at the attached position.

According to the barrel with a cap having such a configuration, as the threaded engagement between the threaded connector-side engaging part and the threaded barrel-side engaging part proceeds, the connector is displaced from the initial position to the attached position, and then the connector is fixed at the attached position. Thus, the connector is directly attached onto the barrel, and therefore when the cap is separated from the nozzle, only the connector detached from the cap remains attached to the barrel.

The barrel with a cap according to the present invention may be configured so that: the cap includes a threaded portion that threadedly engages the threaded portion of the connector when the connector is being displaced from the initial position to the attached position: and the threaded portion of the cap and the threaded portion of the connector are formed so that the threaded engagement with each other is released so as to allow the cap to be detached from the connector when the connector is fixed at the attached position.

According to the barrel with a cap having such a configuration, the cap is provided with a threaded portion that threadedly engages the threaded portion of the connector. When the connector is being displaced from the initial position to the attached position, the threaded portion of the cap and the threaded portion of the connector are threadedly engaged with each other, which can prevent the cap from being detached from the connector so as to prevent separation of the cap from the nozzle.

When the connector is fixed at the attached position, the threaded engagement between the threaded portion of the cap and the threaded portion of the connector is released, thereby allowing the cap to be detached from the connector. It is therefore possible to prevent the cap from being unintentionally separated from the nozzle before the connector is fixed at the attached position.

According to the present invention, there is also provided a pre-filled syringe including: the above-mentioned barrel with a cap; and an elastic gasket to be inserted into the barrel so as to sealingly retain a content filled within the barrel.

According to the present invention, there is further provided a cap with a connector including: a cap to be attached to a nozzle provided at a distal end of a tubular barrel so as to sealingly close the nozzle; and a tubular connector into which the nozzle is inserted, the connector having a threaded portion for threadedly engaging a connection-receiving body to which the nozzle is connected, wherein the connector is detachably coupled to the cap and is separated from the barrel together with the cap at an initial position in which the connector is attached to the barrel via the cap, and the connector includes a connector-side engaging part that engages the barrel when the connector is located at an attached position that is located closer to a proximal end in an axial direction of the barrel than the initial position is, thereby allowing the connector to remain attached to the barrel by being detached from the cap separated from the nozzle.

Advantageous Effects of Invention

As has been described above, the barrel with a cap, the pre-filled syringe, and the cap with a connector according to the present invention exert an excellent effect of being available for both connection-receiving bodies of the Luer lock type and connection-receiving bodies of the slip-in type.

BRIEF DESCRIPTION OF DRAWINGS

FIG. 1(a) is a front view, and FIG. 1(b) is a sectional view taken along the line A-A.

FIG. 2(a) is a plan view, FIG. 2(b) is a front view, FIG. 2(c) is a bottom view, and FIG. 2(d) is a sectional view taken along the line B-B.

FIG. 3(a) is a plan view, FIG. 3(b) is a front view, FIG. 3(c) is a bottom view, and FIG. 3(d) is a sectional view taken along the line C-C.

FIG. 4(a) is a plan view, FIG. 4(b) is a front view, FIG. 4(c) is a bottom view, and FIG. 4(d) is a sectional view taken along the line D-D.

FIGS. 5(a) and 5(b) each are a vertical sectional view of a main part of a barrel with a cap according to the one embodiment, illustrating an action of the barrel with a cap.

FIGS. 7(a) and 7(b) each are a vertical sectional view of a main part of the barrel with a cap according to the one embodiment, illustrating an action of the barrel with a cap.

FIGS. 8(a) and 8(b) each are a vertical sectional view of a main part of a barrel with a cap according to another embodiment of the present invention, where FIG. 8(a) illustrates a state where a connector is located at an initial position, and FIG. 8(b) illustrates a state where the connector is located at an attached position.

FIG. 9(a) is a plan view, FIG. 9(b) is a front view, FIG. 9(c) is a bottom view, and FIG. 9(d) is a sectional view taken along the line E-E.

FIG. 10(a) is a plan view, FIG. 10(b) is a front view, FIG. 10(c) is a bottom view, and FIG. 10(d) is a sectional view taken along the line F-F.

FIG. 11(a) is a plan view, FIG. 11(b) is a front view, FIG. 11(c) is a bottom view, and FIG. 11(d) is a sectional view taken along the line G-G.

FIG. 12(a) is an overall plan view of the barrel, FIG. 12(b) is a front view of a main part of the barrel, FIG. 12(c) is an overall vertical sectional view of a connector, and FIG. 12(d) is an overall bottom view of a connector.

FIGS. 13(a) and 13(b) each are a vertical sectional view of a main part of the barrel with a cap according to the still other embodiment of the present invention, where FIG. 13(a) illustrates a state where a connector is located at the initial position, and FIG. 13(b) illustrates a state where the connector is located at the attached position.

DESCRIPTION OF EMBODIMENTS

Hereinafter, a first embodiment of a pre-filled syringe (a barrel with a cap and a cap with a connector) according to the present invention is described with reference to FIG. 1 to FIG. 7.

Figure 1A:
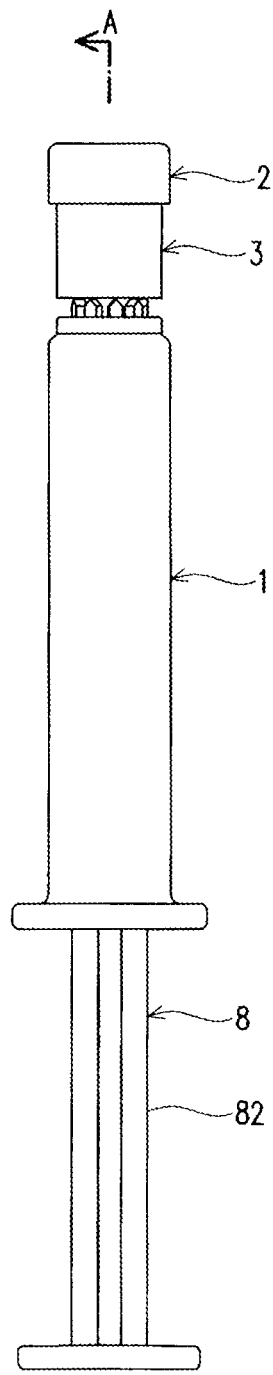
FIGS. 1(a) and 1(b) each show an overall view of a pre-filled syringe according to one embodiment of the present invention, where
Figure 1B:
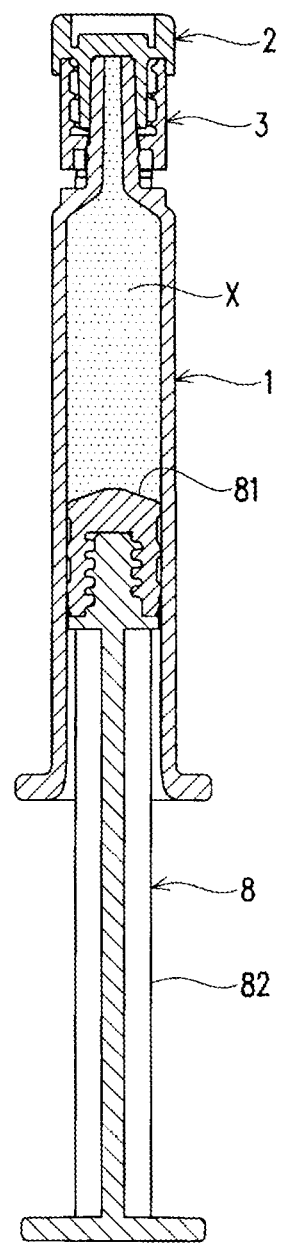
Figure 2A:
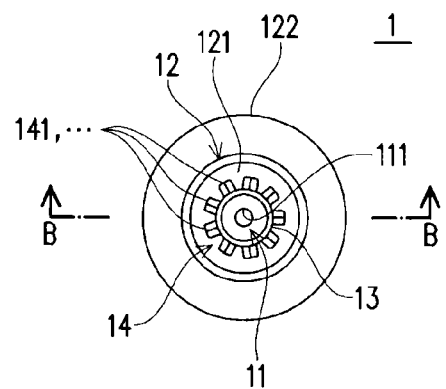
FIGS. 2(a) to 2(d) each show an overall view of a barrel according to the one embodiment, where
Figure 2B:
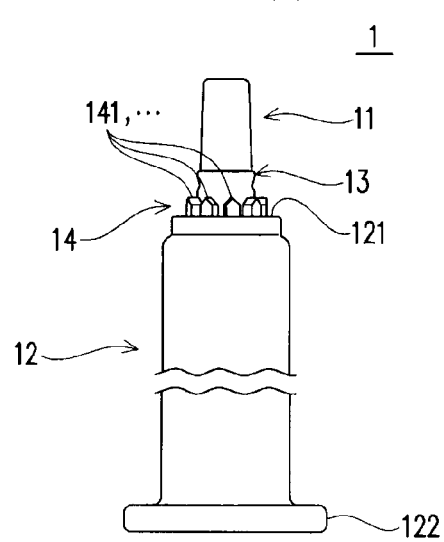
Figure 2D:
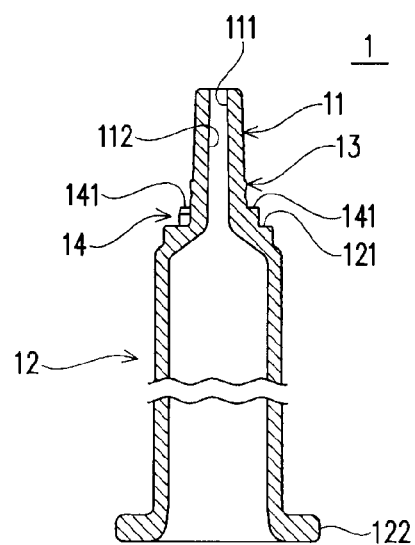
Figure 2C:
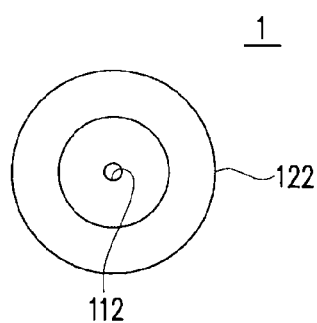
Figure 3A:
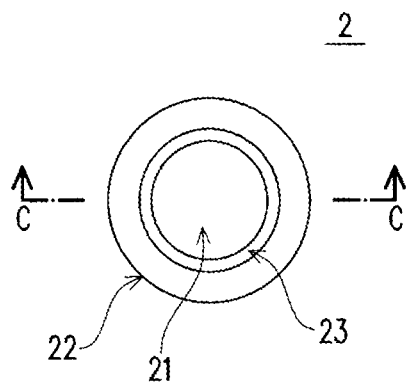
FIGS. 3(a) to 3(d) each show an overall view of a cap according to the one embodiment, where
Figure 3B:
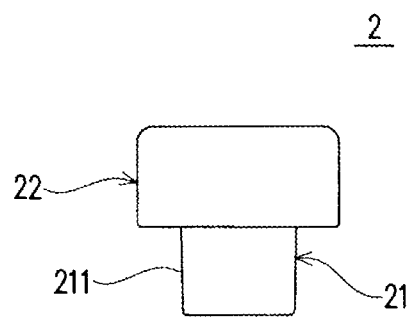
Figure 3D:
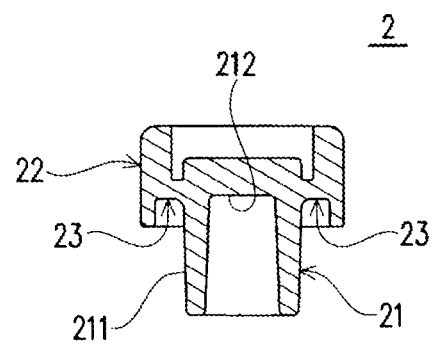
Figure 3C:
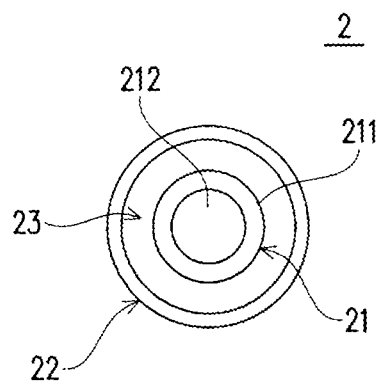
Figure 4A:
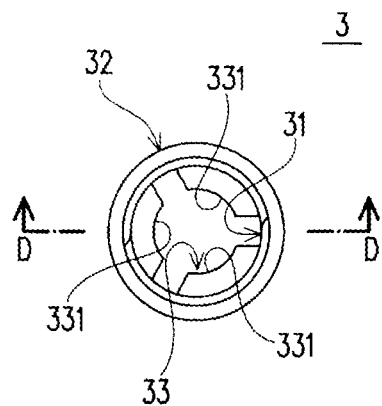
FIGS. 4(a) to 4(d) each show an overall view of a connector according to the one embodiment, where
Figure 4B:
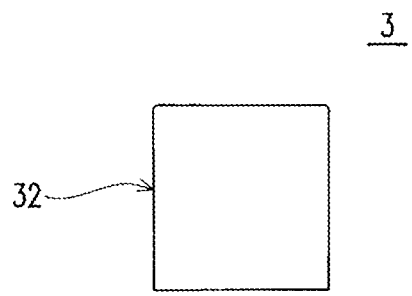
Figure 4D:
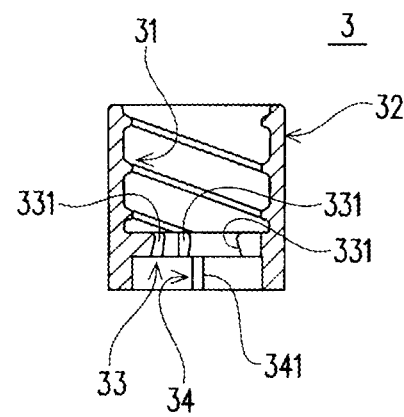
Figure 4C:
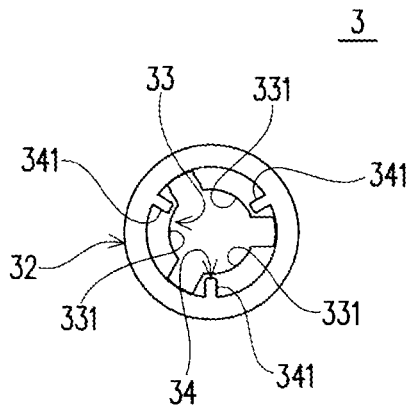

As shown in FIG. 1 to FIG. 4, a pre-filled syringe according to this embodiment includes: a tubular barrel 1 having a nozzle 11 at its distal end; a cap 2 that is attached to the nozzle 11 so as to sealingly close the nozzle 11; and a tubular connector 3 having a threaded portion 31 that threadedly engages a threaded portion of a connection-receiving body (not shown) to be connected to the nozzle 11. It should be noted in the following descriptions that "the upper (side)" of FIG. 1 is referred to as "distal end (side)" or "one (side)", and "the lower (side)" of FIG. 1 is referred to as "proximal end (side)" or "the other (side)".

The pre-filled syringe further includes a plunger 8 that sealingly retains a content X, such as a liquid medicine, filled within the barrel 1. The plunger 8 includes: a gasket 81 having elasticity which is inserted into the barrel 1 and sealingly retains the content X; and a plunger rod 82 having a distal end threadedly connected to the gasket 81.

The pre-filled syringe is configured, though the detail thereof is described later, so that the cap 2 is separated from the nozzle 11 when the connector 3 is located at an initial position, thereby allowing the cap 2 and the connector 3 to be separated integrally from the barrel 1. Furthermore, the pre-filled syringe is configured so that the connector 3 is located at an attached position that is closer to the proximal end in the axial direction of the barrel 1 than the initial position is, which allows the connector 3 to be directly attached onto the barrel 1. Therefore, when the cap 2 is separated from the nozzle 11 in a subsequent step, only the connector 3 detached from the cap 2 remains attached to the barrel 1.

It should be noted that an assembly of the cap 2 and the connector 3 is referred to as a "cap with a connector", and an assembly of the barrel 1 and the cap with a connector (the cap 2 and the connector 3) is referred to as a "barrel with a cap". Further, an assembly of the barrel with a cap (the barrel 1, the cap 2, and the connector 3) and the plunger 8 is referred to as a "syringe".

The barrel 1 includes a tubular barrel body 12 having a distal end to be coupled to the nozzle 11. Further, the barrel 1 includes: a barrel-side engaging part 13 that engages the connector 3 so that the connector 3 is fixed at the attached position; and a rotation-regulating part 14 that regulates the rotation of the connector 3 when being located at the attached position about the axial direction. The barrel 1 is formed, for example, of glass, a hard resin, or the like, so as to have rigidity.

The nozzle 11 includes: at its distal end a discharge opening 111 that discharges the content X filled within the barrel body 12 to the outside; and a communication part 112 that allows communication between the discharge opening 111 and the inside of the barrel body 12 so that the content X flows therethrough. The nozzle 11 is provided in the form of a cylinder protruding from the distal end of the barrel body 12 and formed into a tapered shape so as to have an outer diameter decreasing from its proximal end toward its distal end.

The barrel body 12 includes at its distal end a flat abutting part 121 that abuts against the proximal end of the connector 3. The barrel body 12 further includes at its proximal end a finger catch 122 in the form of a flange which can catch fingers. The barrel body 12 is formed so as to have an outer diameter larger than the outer diameter of the nozzle 11.

The barrel-side engaging part 13 is formed projecting radially outwardly from the outer periphery of the nozzle 11 so as to regulate the movement of the connector 3 in the axial direction by locking the connector 3 in an engaged state in the axial direction. The barrel-side engaging part 13 is provided in the form of a ring extending along the circumferential direction. The barrel-side engaging part 13 is formed into a tapered shape so as to have a diameter gradually decreasing from the distal end side toward the proximal end side. The barrel-side engaging part 13 is arranged on the proximal end side of the nozzle 11.

The rotation-regulating part 14 includes a plurality (nine in this embodiment) of locking pieces 141 projecting radially outwardly from the outer periphery of the nozzle 11 so as to lock the connector 3 in an engaged state in the circumferential direction. The rotation-regulating part 14 is arranged closer to the proximal end than the barrel-side engaging part 13 is. Specifically, the rotation-regulating part 14 is arranged at the proximal end of the nozzle 11.

The plurality of locking pieces 141 are arranged side by side at specific intervals in the circumferential direction. Each locking piece 141 is provided extending along the axial direction. The locking piece 141 is formed so as to have a sharpened distal end.

The cap 2 includes: a sealing part 21 that sealingly closes the nozzle 11; a coupling part 22 that is detachably coupled to the connector 3; and a connecting part 23 that connects the sealing part 21 and the coupling part 22 to each other. The cap 2 is formed, for example, of rubber so as to have elasticity.

The sealing part 21 includes: a tubular sealing body 211 that is fitted around the outer periphery of the distal end of the nozzle 11 so as to be attached to the distal end of the nozzle 11; a seal-closing part 212 that is arranged at the distal end of the sealing body 211 and sealingly closes the discharge opening 111 of the nozzle 11. That is, the sealing part 21 is configured to close the distal end (one end) of the tubular sealing body 211 with the seal-closing part 212.

The coupling part 22 is formed into a cylindrical shape such that its proximal end is fitted around the outer periphery of the distal end of the connector 3. The coupling part 22 is formed so as to have an inner diameter larger than the outer diameter of the sealing part 21 and is arranged so as to accommodate the sealing part 21 thereinside. Further, the coupling part 22, when no force is applied to the cap 2, is arranged so as to accommodate the seal-closing part 212 of the sealing part 21 thereinside, in other words, so that its distal end is located more on one side (distal end side) than the distal end of the sealing part 21 is.

The connecting part 23 connects the outer periphery of the sealing part 21 and the inner periphery of the coupling part 22 to each other. Specifically, the connecting part 23 connects the distal end side of the outer periphery of the sealing part 21 and the proximal end side of the inner periphery of the coupling part 22 to each other. The connecting part 23 elastically deforms, thereby connecting the sealing part 21 and the coupling part 22 in relatively displaceable manner in the axial direction.

The connector 3 includes a tubular connector body 32, along the inner periphery on the distal end side of which the threaded portion 31 in the form of an internal thread is provided. The connector 3 further includes: a connector-side engaging part 33 that engages the barrel-side engaging part 13 of the barrel 1; and a lock-receiving part 34 to be locked to the rotation-regulating part 14 of the barrel 1 in the circumferential direction. The connector 3 is formed, for example, of a hard resin so as to have rigidity.

The connector-side engaging part 33 is arranged on the proximal end side of the connector body 32. The connector-side engaging part 33 further includes a plurality (three in this embodiment) of engaging pieces 331 projecting radially inwardly from the inner periphery of the connector body 32. The plurality of engaging pieces 331 are each provided extending arcuately along the circumferential direction and are arranged side by side at specific intervals in the circumferential direction.

The lock-receiving part 34 is arranged closer to the proximal end than the connector-side engaging part 33 is. Specifically, the lock-receiving part 34 is arranged at the proximal end of the connector body 32. The lock-receiving part 34 further includes a plurality (three in this embodiment) of lock-receiving pieces 341 projecting radially inwardly from the inner periphery of the connector body 32. The plurality of lock-receiving pieces 341 are each provided extending linearly along the axial direction and are arranged side by side at specific intervals in the circumferential direction.

Hereinafter, a method for producing the pre-filled syringe is schematically described. The pre-filled syringe is produced by: filling the content X, such as a liquid medicine, into the barrel 1 in which the nozzle 11 is sealingly closed by the cap 2; then inserting the gasket 81 further into the barrel 1 from the proximal end side; and then coupling the plunger rod 82 to the gasket 81.

The configuration of the pre-filled syringe according to this embodiment is as described above. Next, a method for attaching and detaching the connector of the pre-filled syringe according to this embodiment is described with reference to FIG. 5 to FIG. 7.

First, a method for separating the connector 3 from the barrel 1 is described. As shown in FIG. 5(*a*), the connector 3 when being located at the initial position is attached to the barrel 1 via the cap 2 that is detachably coupled with the connector 3. In such a state, the nozzle 11 of the barrel 1 is inserted (loosely inserted) into the connector 3, and the barrel 1 and the connector 3 do not overlap each other in the axial direction (in plan view) on the distal end side (one end side) of the connector-side engaging part 33, that is, are spaced from each other in the radial direction.

From such a state, when the cap 2 is separated from the nozzle 11 as shown in FIG. 5(*b*), the cap 2 and the connector 3 are integrally separated from the barrel 1. Accordingly, it is possible to connect a connection-receiving body, such as an injection needle and an access port, of the slip-in type (insertion type) to the nozzle 11 of the barrel 1 from which the connector 3 has been separated.

Figure 6A:
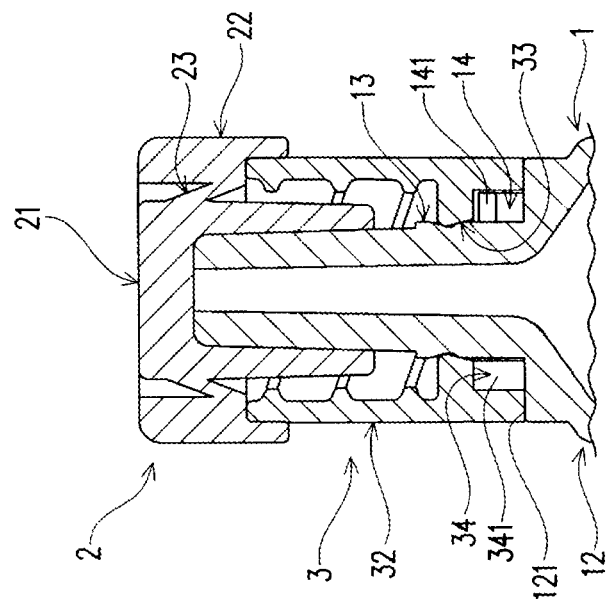
FIGS. 6(a) and 6(b) each are a vertical sectional view of a main part of the barrel with a cap according to the one embodiment, illustrating an action of the barrel with a cap.
Figure 6B:
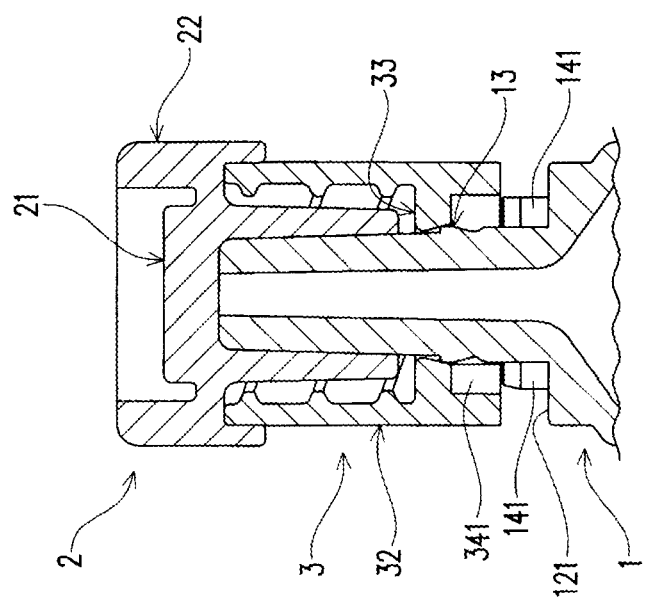
Figure 9A:
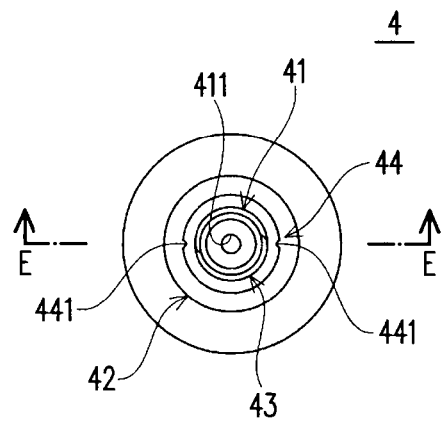
FIGS. 9(a) to 9(d) each show an overall view of the barrel according to the other embodiment, where
Figure 9B:
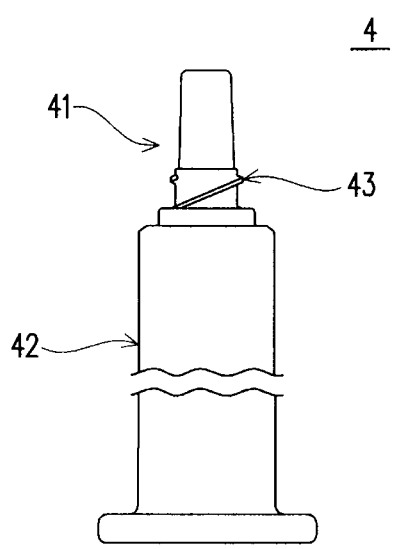
Figure 9D:
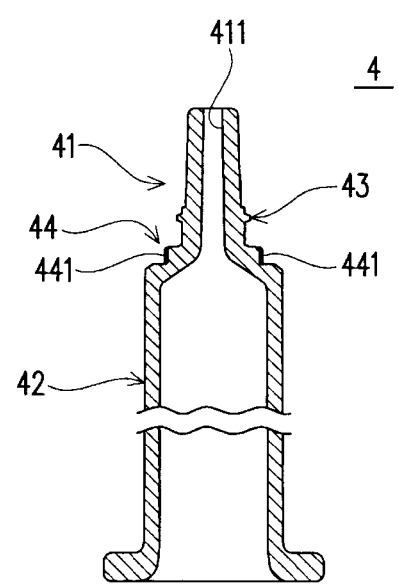
Figure 9C:
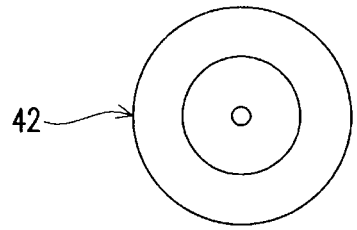
Figure 10A:
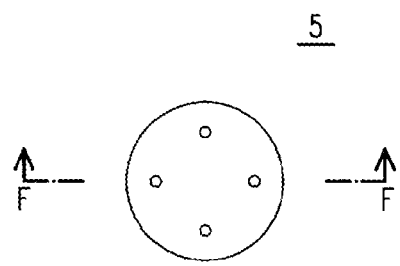
FIGS. 10(a) to 10(d) each show an overall view of the cap according to the other embodiment, where
Figure 10B:
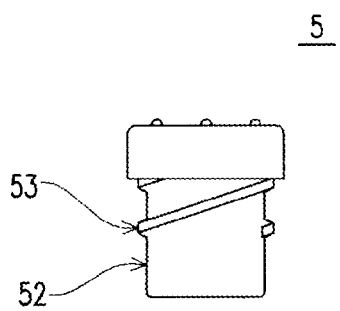
Figure 10D:
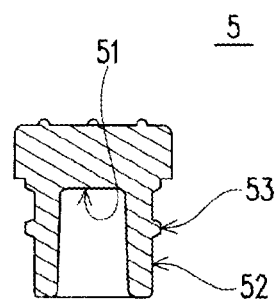
Figure 10C:
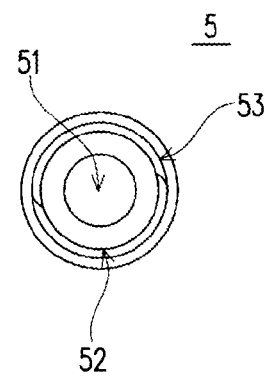
Figure 11A:
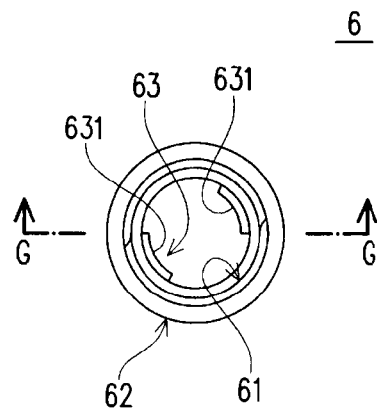
FIGS. 11(a) to 11(d) each show an overall view of a connector according to the other embodiment, where
Figure 11B:
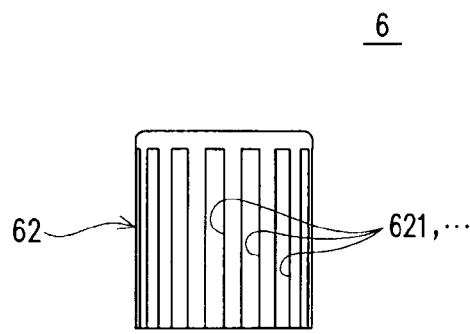
Figure 11D:
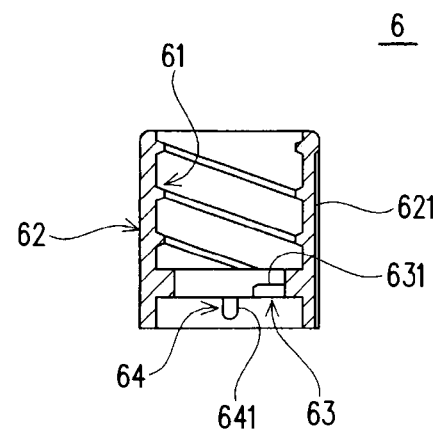
Figure 11C:
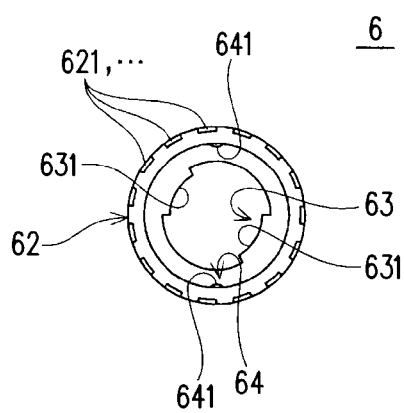

Next, a method for attaching the connector 3 onto the barrel 1 is described. As shown in FIG. 6(*a*), when the connector 3 is located at the initial position, the connector-side engaging part 33 is located more on the one side (distal end side) than the barrel-side engaging part 13 is, and the inner periphery of the connector-side engaging part 33 and the outer periphery of the barrel-side engaging part 13 overlap each other in the axial direction. Further, the distal end of the coupling part 22 is located more on the one side (distal end side) than the distal end of the sealing part 21 is.

From such a state, when the distal end of the cap 2 is pressed by a hand toward the other side (proximal end side), only the coupling part 22 in contact with the hand is pressed toward the other side. Accordingly, as shown in FIG. 6(*b*), the connecting part 23 elastically deforms, thereby allowing the coupling part 22 to move toward the other side relative to the sealing part 21, as well as allowing the connector 3 coupled to the coupling part 22 to move toward the other side relative to the barrel 1 so as to be located at the attached position.

At this time, the connector 3 is pressed down via the coupling part 22, which allows the connector-side engaging part 33 to be located more on the other side (proximal end side) than the barrel-side engaging part 13 is, as well as allowing each lock-receiving piece 341 of the connector 3 to be inserted between two adjacent locking pieces 141 of the rotation-regulating part 14. In this embodiment, the connector 3 is located at the attached position when the distal end of the coupling part 22 and the distal end of the sealing part 21 are located on the same plane.

When the connector 3 is located at the attached position, the proximal end of the connector body 32 is abutted against the abutting part 121 of the barrel body 12 from the other side (proximal end side), and the connector-side engaging part 33 is locked to the barrel-side engaging part 13 from the one side (distal end side). In this way, the movement of the connector 3 in the axial direction is regulated. Further, each lock-receiving piece 341 of the lock-receiving part 34 is locked to the locking piece 141 of the rotation-regulating part 14 in the circumferential direction. Thus, the rotation of the connector 3 about the axial direction is regulated.

When the pressure on the cap 2 is released, as shown in FIG. 7(*a*), the connecting part 23 is returned by its elastic force, and the coupling part 22 is moved toward the one side (distal end side) relative to the sealing part 21. At this time, since the connector-side engaging part 33 is locked to the barrel-side engaging part 13 from the one side (distal end side), the connector 3 remains located at the attached position, so that the cap 2 and the connector 3 are detached from each other.

It should be noted that, in the case where the coupling force between the cap 2 and the connector 3 is strong, the state shown in FIG. 6(*b*) is maintained in some cases even when the pressure on the cap 2 is released. Even in such a state, the connector-side engaging part 33 is locked to the barrel-side engaging part 13 from the one side (distal end side), the cap 2 and the connector 3 are in a detachable state.

From such a state, as shown in FIG. 7(*b*), when the cap 2 is separated from the nozzle 11, only the cap 2 is separated from the nozzle 11, while the connector 3 remains attached to the barrel 1. Accordingly, it is possible to connect the connection-receiving body to the nozzle 11 of the barrel 1, from which the cap 2 has been separated, by screwing the threaded portion 31 of the connector 3 into the threaded portion of the connection-receiving body, such as an injection needle and an access port, of the Luer lock type (screw-in).

As can be seen from the above, according to the pre-filled syringe of this embodiment, the connector 3 is attached to the barrel 1 via the cap 2, when the connector 3 is located at the initial position. Thus, the connector 3 is separated from the barrel 1 integrally with the cap 2, when the cap 2 is separated from the nozzle 11.

Meanwhile, when the connector 3 is located at the attached position, the connector-side engaging part 33 engages the barrel-side engaging part 13, and thus the connector 3 is directly attached onto the barrel 1 without the intermediation of the cap 2. This allows only the connector 3 detached from the cap 2 to remain attached to the barrel 1, when the cap 2 is separated from the nozzle 11.

Accordingly, in the case of connection-receiving bodies of the slip-in type, the connector 3 can be separated integrally with the cap 2 by separating the cap 2 from the nozzle 11 when the connector 3 is located at the initial position. Meanwhile, in the case of connection-receiving bodies of the Luer lock type, only the connector 3 can be attached to the barrel 1 by locating the connector 3 at the attached position so that the connector 3 is directly attached onto the barrel 1 and thereafter separating the cap 2 from the nozzle 11. In such a way, the pre-filled syringe of this embodiment is available for both connection-receiving bodies of the slip-in type and connection-receiving bodies of the Luer lock type.

Moreover, in the case of connecting a connection-receiving body of the Luer lock type to the nozzle 11, it is possible to prevent the connection receiving body from being connected to the nozzle 11, with the connector 3 having a clearance for movement or being loosened with respect to the barrel 1, by attaching the connector 3 to the barrel 1 immediately before the connection receiving body is connected to the nozzle 11. Accordingly, the connection-receiving body can be securely connected to the nozzle 11.

Also, according to the pre-filled syringe of this embodiment, the connector 3 is pressed down from the initial position to the attached position, whereby the barrel-side engaging part 13 engages the connector-side engaging part 33. Thus, the barrel-side engaging part 13 locks the connector-side engaging part 33 in the axial direction, so that the connector 3 is fixed at the attached position. This allows the connector 3 to be directly attached onto the barrel 1. Therefore, when the cap 2 is separated from the nozzle 11, only the connector 3 detached from the cap 2 remains attached to the barrel 1.

Further, according to the pre-filled syringe of this embodiment, when the connector 3 is located at the attached position, the rotation-regulating part 14 locks the lock-receiving part 34 in the circumferential direction. This regulates the rotation of the connector 3 about the axial direction with respect to the barrel 1, so that the connector 3 is fixed at the attached position without having a clearance for movement.

Moreover, according to the pre-filled syringe of this embodiment, the sealing part 21 that sealingly closes the nozzle 11 and the coupling part 22 that is detachably coupled to the connector 3 are connected to each other via the connecting part 23 in relatively displaceable manner in the axial direction of the barrel 1. Thus, when the connector 3 is pressed down from the initial position to the attached position, the coupling part 22 is relatively displaced in the axial direction of the barrel 1 with respect to the sealing part 21.

As a result, the connector 3 can be displaced from the initial position to the attached position with the sealing part 21 sealingly closing the nozzle 11. Accordingly, when the connector 3 is attached to the barrel 1, the sealing part 21 keeps sealingly closing the nozzle 11, which can prevent leakage of the content X through the nozzle 11.

Next, a second embodiment of a pre-filled syringe (a barrel with a cap, or a cap with a connector) according to the present invention is described with reference to FIG. 8 to FIG. 11.

As shown in FIG. 8 to FIG. 11, the pre-filled syringe according to this embodiment includes: a tubular barrel 4 having a nozzle 41 at its distal end; a cap 5 that is attached to the nozzle 41 so as to sealingly close the nozzle 41; a tubular connector 6 having a threaded portion 61. (hereinafter, referred to also as a "connector-side threaded portion") that threadedly engages a connection-receiving body (not shown) connected to the nozzle 4L and a plunger 8 (see FIG. 1) that sealingly retains the content such as a liquid medicine filled within the barrel 4.

The pre-filled syringe is configured, though the detail thereof is described later, so that the cap 5 is separated from the nozzle 41 when the connector 6 is located at an initial position, thereby allowing the cap 5 and the connector 6 to be integrally separated from the barrel 4. Furthermore, the pre-filled syringe is configured so that the connector 6 is directly attached onto the barrel 4 by locating the connector 6 at an attached position that is closer to the proximal end in the axial direction of the barrel 4 than the initial position is, and thus when the cap 5 is separated from the nozzle 41 in a subsequent step, only the connector 6 detached from the cap 5 remains attached to the barrel 4.

The barrel 4 includes: a tubular barrel body 42 having a distal end to be coupled to the nozzle 41; a barrel-side engaging part 43 that engages the connector 6 so that the connector 6 is fixed at the attached position; and a rotation-regulating part 44 that regulates the rotation of the connector 6 when being located at the attached position about the axial direction. The barrel 1 is formed so as to have rigidity. The nozzle 41 and the barrel body 42 have substantially the same configurations respectively as the nozzle 11 and the barrel body 12 according to the first embodiment.

The barrel-side engaging part 43 is threaded so as to cause the connector 6 to be displaced from the initial position to the attached position, as the threaded engagement with the connector 6 proceeds, so that the connector 6 is fixed at the attached position. The barrel-side engaging part 43 is arranged along the outer periphery on the proximal end side of the nozzle 41. That is, the barrel-side engaging part 43 is externally threaded.

The rotation-regulating part 44 includes a plurality (two in this embodiment) of recessed locking parts 441 on the outer periphery of the nozzle 41 so as to lock the connector 6 in the circumferential direction. The rotation-regulating part 44 is arranged closer to the proximal end than the barrel-side engaging part 43 is. Specifically, the rotation-regulating part 44 is arranged at the proximal end of the nozzle 41.

The cap 5 includes: a sealing part 51 that sealingly closes a discharge opening 411 of the nozzle 41; a cylindrical cap body 52 that is fitted around the outer periphery of the distal end of the nozzle 41 so as to be attached to the distal end of the nozzle 41; and a threaded portion 53 (hereinafter referred to also as a "cap-side threaded portion") that threadedly engages a connector-side threaded portion 61 so as to be detachably coupled to the connector 6. The cap 5 is formed so as to have elasticity.

The cap-side threaded portion 53 is arranged along the outer periphery on the distal end side of the cap body 52. That is, the cap-side threaded portion 53 is externally threaded. The cap-side threaded portion 53 is formed so as to have the same pitch as the threaded barrel-side engaging part 43.

The connector 6 includes a tubular connector body 62, along the inner periphery on the distal end side of which the connector-side threaded portion 61 in the form of an internal thread is provided. The connector 6 further includes: a connector-side engaging part 63 that is threaded so as to engage the barrel-side engaging part 43; and a lock-receiving part 64 to be locked to the rotation-regulating part 44 in the circumferential direction. The connector 6 is formed so as to have rigidity.

The connector-side threaded portion 61 threadedly engages the cap-side threaded portion 53, thereby causing displacement of the connector 6 from the initial position to the attached position. The connector-side threaded portion 61 and the cap-side threaded portion 53 are each configured so as to have a length of screw thread set so that their thread engagement is released when the connector 6 has been fixed at the attached position.

The connector body 62 has an outer periphery provided with a plurality of groove portions 621 extending linearly along the axial direction. Specifically, the connector body 62 is formed so that the outer periphery has projections and recesses in the circumferential direction, which are formed by the plurality of groove portions 621 arranged side by side on the outer periphery in the circumferential direction. This allows fingers of the user to hold the outer periphery of the connector body 62 in a non-slip manner when the connector 6 is rotationally moved by the fingers, thereby preventing the fingers from slipping on the outer periphery of the connector body 62.

The connector-side engaging part 63 is arranged on the proximal end side of the connector body 62. Also, the connector-side engaging part 63 is in the form of a thread that threadedly engages the barrel-side engaging part 43 so as to regulate the movement of the connector 6 in the axial direction by being locked to the barrel-side engaging part 43 in the axial direction.

Specifically, the connector-side engaging part 63 includes a plurality (two in this embodiment) of engaging pieces 631 projecting radially inwardly from the inner periphery of the connector body 62 so as to threadedly engage the barrel-side engaging part 43. The plurality of engaging pieces 631 are each provided extending arcuately along the circumferential direction and are arranged side by side at specific intervals in the circumferential direction.

The lock-receiving part 64 is arranged closer to the proximal end than the connector-side engaging part 63 is. Specifically, the lock-receiving part 64 is arranged at the proximal end of the connector body 62. The lock-receiving part 64 further includes a plurality (two in this embodiment) of lock-receiving pieces 641 projecting radially inwardly from the inner periphery of the connector body 62. The plurality of lock-receiving pieces 641 are each provided extending linearly along the axial direction and are arranged side by side at specific intervals in the circumferential direction.

The configuration of the pre-filled syringe according to this embodiment is as described above. Next, a method for attaching and detaching the connector of the pre-filled syringe according to this embodiment is described with reference to FIG. 8.

As shown in FIG. 8(a), when the connector 6 is located at the initial position, the connector 6 is attached to the barrel 4 via the cap 5 that is detachably coupled to the connector 6. In such a state, while the connector-side threaded portion 61 and the cap-side threaded portion 53 are threadedly engaged with each other, the connector-side engaging part 63 and the barrel-side engaging part 43 are not threadedly engaged or not engaged with each other.

From such a state, when the cap 5 is separated from the nozzle 41, the cap 5 and the connector 6 are integrally separated from the barrel 4. Thus, it is possible to connect a connection-receiving body of the slip-in type to the nozzle 41 of the barrel 4 from which the connector 6 has been separated.

As shown in FIG. 8(a), when the connector 6 is located at the initial position, the connector-side engaging part 63 is located more on the one side (distal end side) than the barrel-side engaging part 43 is. In such a state, the nozzle 41 of the barrel 4 is inserted into the connector 6.

From such a state, as the connector 6 is rotated about the axial direction, the connector-side engaging part 63 that is internally threaded and the barrel-side engaging part 43 that is externally threaded are threadedly engaged with each other in a direction in which they are tightened together, whereas the connector-side threaded portion 61 that is internally threaded and the cap-side threaded portion 53 that is externally threaded are threadedly engaged with each other in a direction in which they are loosened. Following this, the connector 6 is displaced from the initial position to the attached position.

At this time, when the connector 6 is being displaced from the initial position to the attached position, since the cap-side threaded portion 53 and the connector-side threaded portion 61 are threadedly engaged with each other, the connector-side threaded portion 61 locks the cap-side threaded portion 53 in the axial direction. Accordingly, the cap 5 is not detached from the connector 6 and thus is not separated from the nozzle 41.

Furthermore, when the connector 6 is rotated about the axial direction, as shown in FIG. 8(b), the connector 6 moves toward the other side relative to the barrel 4, so as to be located at the attached position. At this time, each lock-receiving piece 641 in the form of a projection of the lock-receiving part 64 is fitted to each locking part 441 in the form of a recess of the rotation-regulating part 44. Thus, the lock-receiving piece 641 of the lock-receiving part 64 is locked to the locking part 441 of the rotation-regulating part 44 in the circumferential direction. Thereby the rotation of the connector 6 about the axial direction is regulated, which can prevent the barrel-side engaging part 43 and the connector-side engaging part 63 from being loosened.

When the connector 6 is located at the attached position, the barrel-side engaging part 43 and the connector-side engaging part 63 are threadedly engaged with each other, and therefore the connector-side engaging part 63 is locked to the barrel-side engaging part 43 in the axial direction. Accordingly the movement of the connector 6 is regulated in the axial direction, and thus the connector 6 is fixed at the attached position.

Furthermore, when the connector 6 is fixed at the attached position, the threaded engagement between the cap-side threaded portion 53 and the connector-side threaded portion 61 is released, and thus the cap 5 can be detached from the connector 6. Accordingly, when the cap 5 is separated from the nozzle 41, only the connector 6 detached from the cap 5 remains attached to the barrel 4. In this way, it is possible to connect a connection-receiving body of the Luer lock type to the nozzle 41 of the barrel 4, from which the cap 5 has been separated, by allowing the connector-side threaded portion 61 to threadedly engage the threaded portion of the connection-receiving body.

As can be seen from the above, according to the pre-filled syringe of this embodiment, the connector 6 is separated from the barrel 4 integrally with the cap 5 by separating the cap 5 from the nozzle 41 when the connector 6 is located at the initial position, whereas only the connector 6 detached from the cap 5 remains attached to the barrel 4 by separating the cap 5 from the nozzle 41 after the connector 6 is directly attached onto the barrel 4 without the intermediation of the cap 5 when the connector 6 is located at the attached position. Accordingly, the pre-filled syringe of this embodiment is available for both connection-receiving bodies of the slip-in type and connection-receiving bodies of the Luer lock type.

Further, according to the pre-filled syringe of this embodiment, as the threaded engagement between the connector-side engaging part 63 that is internally threaded and the barrel-side engaging part 43 that is externally threaded proceeds, the connector 6 is displaced from the initial position to the attached position, and the connector 6 is thereafter fixed at the attached position. Thus, the connector 6 is directly attached onto the barrel 4. Therefore, when the cap 5 is separated from the nozzle 41, only the connector 6 detached from the cap 5 remains attached to the barrel 4.

Further, according to the pre-filled syringe of this embodiment, when the connector 6 is being displaced from the initial position to the attached position, the cap-side threaded portion 53 and the connector-side threaded portion 61 are threadedly engaged with each other. Therefore, the cap 5 cannot be separated from the nozzle 41 by being detached from the connector 6. This makes it possible to forcibly maintain the state where the nozzle 41 is sealingly closed by the sealing part 51.

When the connector 6 is fixed at the attached position, the threaded engagement between the cap-side threaded portion 53 and the connector-side threaded portion 61 is released, thereby allowing the cap 5 to be detached from the connector 6. It is therefore possible to prevent the cap 5 from being separated from the nozzle 41 before the connector 6 is fixed at the attached position. Accordingly, leakage of the content through the nozzle 41 can be prevented, since the nozzle 41 is kept sealingly closed by the sealing part 51 during the time the connector 6 is being displaced from the initial position to the attached position.

It is a matter of course that the pre-filled syringe, the barrel with a cap, and the cap with a connector according to the present invention are not limited to the above-mentioned embodiments, and various modifications can be made without departing from the gist of the present invention. It is also possible to arbitrarily employ and combine configurations, methods, etc., of each of the aforementioned plurality of embodiments (or to apply configurations, methods, etc., according to one embodiment to the configurations, methods, etc., according to another embodiment). Further, it is of course possible to arbitrarily select configurations, methods, etc., according to various modifications mentioned below and apply them to the configurations, methods, etc., according to the aforementioned embodiments.

For example, in the pre-filled syringe, the barrel with a cap, and the cap with a connector according to the above-mentioned embodiments, a configuration in which the threaded portion 31, 61 of the connector 3, 6 that is internally threaded along the inner periphery of the connector body 32, 62 threadedly engages the externally threaded connection-receiving body of the Luer lock type is described herein, which however is not restrictive. Specifically, the threaded portion of the connector may be externally threaded along the outer periphery of the connector body so as to threadedly engage an internally threaded connection-receiving body of the Luer lock type.

Further, in the pre-filled syringe, the barrel with a cap, and the cap with a connector according to the above-mentioned embodiments, a configuration in which the barrel-side engaging part 13, 43 projects radially outwardly from the barrel body 12, 42, while the connector-side engaging part 33, 63 projects radially inwardly from the connector body 32, 62 is described herein, which however is not restrictive.

Specifically, the connector-side engaging part may be configured to project radially outwardly from the connector body, while the barrel has a portion that is arranged radially outwardly of the connector body, so that the barrel-side engaging part projects radially inwardly from such a portion.

Further, in the pre-filled syringe according to the above-mentioned embodiments, a configuration in which the plunger 8 (the gasket 81 and the plunger rod 82) is provided inside the barrel 1, 4 is described herein, which however is not restrictive. For example, the pre-filled syringe may be configured to have only the gasket 81 provided inside the barrel 1, 4.

Further, in the pre-filled syringe, the barrel with a cap, and the cap with a connector according to the above-mentioned first embodiment, a configuration in which each lock-receiving piece 341 of the lock-receiving part 34 of the connector 3 is inserted between each two adjacent locking pieces 141 of the rotation-regulating part 14 of the barrel 1 when the connector 3 is displaced from the initial position to the attached position, so that the rotation of the connector 3 at the attached position about the axial direction is regulated is described herein, which however is not restrictive.

For example, each locking piece of the rotation-regulating part is provided further extending linearly along the axial direction toward the distal end side, so that each lock-receiving piece 34 of the connector 3 is inserted between the locking pieces of the rotation-regulating part also when the connector 3 is located at the initial position. With such a configuration, the rotation of the connector 3 about the axial direction is regulated from the time the connector 3 is located at the initial position to the time it is located at the attached position. Further, during the time the connector 3 is being displaced from the initial position to the attached position, each lock-receiving piece 34 of the connector 3 is guided by the locking pieces of the rotation-regulating part, and damage due to interference therebetween can be prevented.

As still another example of modification, as shown in FIG. 12 and FIG. 13, there is a configuration in which at least either one of a barrel 1a and a connector 3a is plastically deformed when the connector 3a is displaced from the initial position to the attached position, so that the rotation of the connector 3a when being located at the attached position about the axial direction is regulated.

This configuration can eliminate the need to determine the position of the connector 3a in the circumferential direction with respect to the barrel 1a when the connector 3a is located at the initial position, and makes it possible to regulate the rotation of the connector 3a when being located at the attached position about the axial direction only by displacing the connector 3a from the initial position to the attached position. Such a configuration is described below.

Figure 12A:
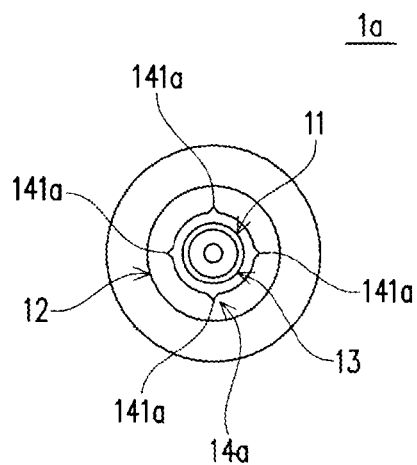
FIGS. 12(a) to 12(d) each show a component view of a barrel with a cap according to still another embodiment of the present invention, where
Figure 12B:
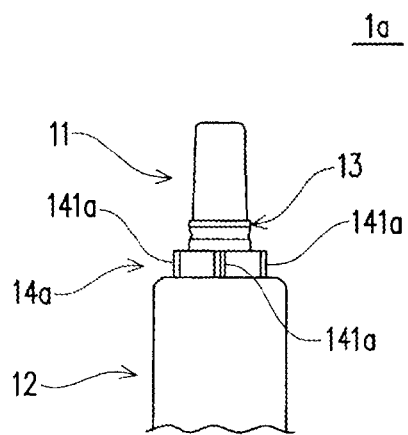

The barrel 1a shown in FIGS. 12(a) and 12(b) includes a rotation-regulating part 14a composed of a plurality (four in FIG. 12 and FIG. 13) of locking pieces 141a projecting radially outwardly from the outer periphery of the nozzle 11 in order to lock the connector 3a in the circumferential direction. The plurality of locking pieces 141a are arranged side by side at specific intervals in the circumferential direction. Further, the locking pieces 141a are each provided extending linearly along the axial direction and formed so as to have a sharpened distal end in the radial direction.

Figure 12C:
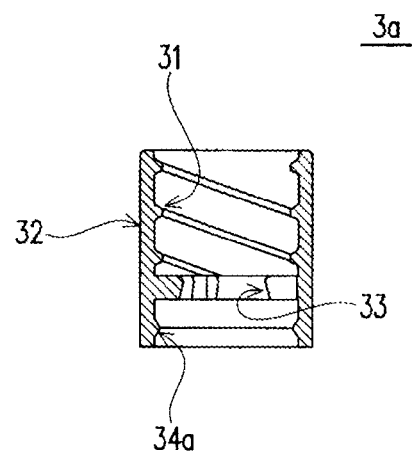
Figure 12D:
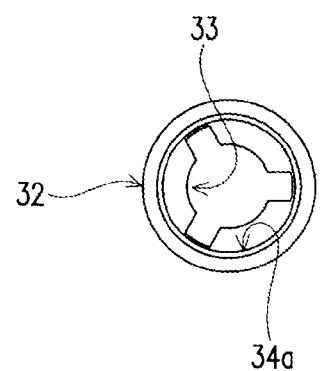

The connector 3a shown in FIGS. 12(c) and 12(d) includes a lock-receiving part 34a projecting radially inwardly from the inner periphery of the connector body 32. The lock-receiving part 34a is provided extending along the circumferential direction in the form of a ring, and is formed, having a sharpened distal end in the radial direction, so as to be plastically deformed by a small force when being brought into pressure contact with the locking pieces 141a of the rotation-regulating part 14a. Further, the lock-receiving part 34a is formed so as to have an inner diameter smaller than the diameter of a circle that circumscribes the respective locking pieces 141a of the rotation-regulating part 14a.

The connector 3a is made of a softer material than the barrel 1a so as to be plastically deformed by interference with the barrel 1a when being displaced to the attached position. For example, in the case where the barrel 1a is made of a resin such as COP (cyclo-olefin polymer) and COC (cyclo-olefin copolymer), the connector 3a is made of a softer resin than those such as PP (polypropylene) and PE (polyethylene). On the other hand, in the case where the barrel 1a is made of a resin such as PP, the connector 3a is made of a softer resin than it such as PE (polyethylene).

As shown in FIG. 13(a), when the connector 3a is located at the initial position, the lock-receiving part 34a of the connector 3a and each locking piece 141a of the rotation-regulating part 14a of the barrel 1a overlap each other in the axial direction. From such a state, the cap 2 is pressed so that the connector 3a is displaced from the initial position to the attached position.

Then, as shown in FIG. 13(b), when the connector 3a is displaced to the attached position, the lock-receiving part 34a of the connector 3a is brought into pressure contact with (forced into) each locking piece 141a of the rotation-regulating part 14a of the barrel 1a, and therefore the lock-receiving part 34a of the connector 3a which is made of a softer resin than the barrel 1a is plastically deformed.

Specifically, the lock-receiving part 34a of the connector 3a is plastically deformed in such a manner that the sharpened distal end of the lock-receiving part 34a collapses. Thus, the lock-receiving part 34a that has been plastically deformed is locked to each locking piece 141a of the rotation-regulating part 14 in the circumferential direction, so that the rotation of the connector 3a when being located at the attached position about the axial direction is regulated.

Moreover, since the connector 3a is made of a softer material than the barrel 1a, deformation of the barrel 1a can be prevented by plastic deformation of the connector 3a. As a result, leakage of the filling liquid due to damage of the barrel 1a can be prevented. Alternatively, it is also possible to employ a configuration in which the barrel 1a and the connector 3a are made of the same material so that the barrel 1a and the connector 3a are plastically deformed, or a configuration in which the connector 3a is made of a harder material than the barrel 1a so that the barrel 1a is plastically deformed.

Further, in the pre-filled syringe, the barrel with a cap, and the cap with a connector according to the above-mentioned first embodiment, a configuration in which the connecting part 23 connects the sealing part 21 and is the coupling part 22 in relatively displaceable manner in the axial direction of the barrel 1, thereby coupling the connector 3 and the coupling part 22 to each other also when the connector 3 is being displaced to the attached position is described herein, which however is not restrictive. Specifically, the configuration may be such that the cap and the connector are detached from each other when the connector is being displaced to the attached position.

Further, in the pre-filled syringe, the barrel with a cap, and the cap with a connector according to the above-mentioned first embodiment, a configuration in which the proximal end of the connector body 32 is abutted against the abutting part 121 of the barrel body 12 from the other side (proximal end side), and the connector-side engaging part 33 is locked to the barrel-side engaging part 13 from the one side (distal end side), thereby regulating the movement of the connector 3 in the axial direction is described herein, which however is not restrictive.

For example, it is also possible to employ a configuration in which the connector-side engaging part is locked to the barrel-side engaging part not only from the one side (distal end side) and but also from the other side (proximal end side), thereby regulating the movement of the connector in the axial direction.

Further, in the pre-filled syringe, the barrel with a cap, and the cap with a connector according to the above-mentioned second embodiment, a configuration in which the cap 5 includes the threaded portion 53 that threadedly engages the threaded portion 61 of the connector 6 is described herein, which however is not restrictive. For example, the cap may be provided without such a threaded portion.

Further, in the pre-filled syringe, the barrel with a cap, and the cap with a connector according to the above-mentioned second embodiment, a configuration in which the threaded portion 53 of the cap 5 and the barrel-side engaging part 43 are formed so as to have the same thread pitch is described herein, which however is not restrictive. Specifically, the threaded portion of the cap and the barrel-side engaging part 43 may be formed so as to have different thread pitches.

In such a configuration, the connector 6 is displaced with respect to the barrel 4 according to the pitch difference between the barrel-side engaging part 43 having rigidity and the connector-side engaging part 63 having rigidity. Accordingly, the threaded portion 61 of the connector 6 and the threaded portion of the cap are threadedly engaged with each other in such a manner that the thread ridge of the threaded portion 61 of the connector 6 having rigidity rides over the thread ridge of the threaded portion of the cap having elasticity, that is, the threaded portion 61 of the connector 6 causes elastic deformation of the threaded portion of the cap.

Further, in the pre-filled syringe, the barrel with a cap, and the cap with a connector according to the above-mentioned second embodiment, a configuration in which the threaded engagement between the threaded portion 61 of the connector 6 and the threaded portion 53 of the cap 5 is released when the connector 6 is fixed at the attached position is described herein, which however is not restrictive.

For example, it is also possible to employ a configuration in which the threaded portion of the connector and the threaded portion of the cap are threadedly engaged with each other even when the connector is fixed at the attached position, from the state of which the cap is further rotated so that the threaded portion of the connector and the threaded portion of the cap are threadedly engaged with each other in a direction in which they are loosened, thereby releasing the threaded engagement between the threaded portion of the cap and the threaded portion of the connector, so that the cap can be separated from the nozzle.

According to such a configuration, it is possible to easily separate the cap from the nozzle by rotating (while twisting), instead of pulling, the cap, when the cap made of a material such as rubber is held in close contact with the nozzle. Thus, this configuration can force the separation of the cap from the nozzle when needed.

REFERENCE SIGNS LIST

1: Barrel
1a: Barrel
2: Cap
3: Connector
3a: Connector
4: Barrel
5: Cap
6: Connector
8: Plunger
11: Nozzle
13: Barrel-side engaging part
21: Sealing part
22: Coupling part
23: Connecting part
31: Threaded portion
33: Connector-side engaging part
41: Nozzle
43: Barrel-side engaging part
61: Threaded portion
63: Connector-side engaging part
81: Gasket
X: Content

The invention claimed is:

1. A barrel with a cap, comprising:
a tubular barrel having a nozzle at its distal end;
a cap to be attached to the nozzle so as to sealingly close the nozzle; and
a tubular connector into which the nozzle is inserted, the connector having a threaded portion for threadedly engaging a connection-receiving body to be connected to the nozzle, wherein
the connector is detachably coupled to the cap and is separated from the barrel together with the cap when the connector is located at an initial position in which the connector is attached to the barrel via the cap with the nozzle sealingly closed by the cap, and
the connector comprises a connector-side engaging part that engages the barrel when the connector is located at an attached position that is located closer to a proximal end in an axial direction of the barrel than the initial position is, thereby allowing the connector to remain attached to the barrel by being detached from the cap separated from the nozzle.

2. The barrel with the cap according to claim 1, wherein the barrel comprises a barrel-side engaging part that engages the connector-side engaging part when the connector is pressed down from the initial position to the attached position, thereby allowing the connector to be fixed at the attached position.

3. The barrel with the cap according to claim 2, wherein the cap comprises: a sealing part that sealingly closes the nozzle; a coupling part that is coupled to the connector; and a connecting part that connects the sealing part and the coupling part to each other in a relatively displaceable manner in the axial direction of the barrel.

4. The barrel with the cap according to claim 1, wherein the connector-side engaging part is threaded, and
the barrel comprises a barrel-side engaging part that is threaded so as to cause the connector to be displaced from the initial position to the attached position, as threaded engagement between the barrel-side engaging part and the connector-side engaging part proceeds, so that the connector is fixed at the attached position.

5. The barrel with the cap according to claim 4, wherein the cap comprises a threaded portion that threadedly engages a connector-side threaded portion of the connector when the connector is being displaced from the initial position to the attached position, and
the threaded portion of the cap and the connector-side threaded portion of the connector are formed so that threaded engagement with each other is released so as to allow the cap to be detached from the connector when the connector is fixed at the attached position.

6. A pre-filled syringe comprising:
the barrel with the cap according to claim 1; and
an elastic gasket to be inserted into the barrel so as to sealingly retain a content filled within the barrel.

7. A cap with a connector, comprising:
the cap to be attached to a nozzle provided at a distal end of a tubular barrel so as to sealingly close the nozzle;
a tubular connector into which the nozzle is intended to be inserted, the connector having a threaded portion for threadedly engaging a connection-receiving body to which the nozzle is intended to be connected, wherein
the connector is detachably coupled to the cap and is separated from the barrel together with the cap at an initial position in which the connector is attached to the barrel via the cap with the nozzle sealingly closed by the cap, and
the connector comprises a connector-side engaging part that engages the barrel when the connector is located at an attached position that is located closer to a proximal end of the barrel in an axial direction of the barrel than the initial position is, thereby allowing the connector to remain attached to the barrel by being detached from the cap separated from the nozzle.

* * * * *